United States Patent [19]

Boyle

[11] Patent Number: 5,006,543
[45] Date of Patent: Apr. 9, 1991

[54] DIPHENYLETHANE DERIVATIVES

[75] Inventor: Francis T. Boyle, Congleton, England

[73] Assignee: Imperial Chemical Industries PLC, London, England

[21] Appl. No.: 384,487

[22] Filed: Jul. 25, 1989

[30] Foreign Application Priority Data

Aug. 4, 1988 [GB] United Kingdom ............. 8818561.6

[51] Int. Cl.$^5$ ..................... A61K 31/41; C07D 249/08
[52] U.S. Cl. ................................. 514/383; 548/262.2; 548/267.4
[58] Field of Search ..................... 514/383; 548/262.2, 548/267.4

[56] References Cited

U.S. PATENT DOCUMENTS 4,598,085  7/1986  Hares et al. ...................... 548/262.2

FOREIGN PATENT DOCUMENTS 1601423  10/1981  United Kingdom ............. 548/262.2

Primary Examiner—Mary C. Lee
Assistant Examiner—Patricia L. Morris
Attorney, Agent, or Firm—Cushman, Darby & Cushman

[57] ABSTRACT

Diphenylethane derivatives of the formula

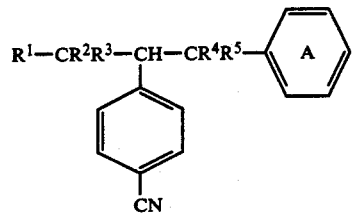

are described;
wherein $R^1$ is a heterocyclyl radical selected from the group consisting of 1,2,4-triazolyl, optionally-substituted imidazolyl, pyridyl and pyrimidinyl radicals; $R^2$ and $R^3$, which may be the same or different, are each a hydrogen atom or a 1-6C alkyl radical; $R^4$ and $R^5$, which may be the same or different, are each a hydrogen or fluorine atom or a 1-6C alkyl radical; and A is a phenyl radical, optionally bearing one or more substituents selected from halogen atoms, cyano radicals or 1-4C halogenoalkyl or halogenoalkoxy radicals. Processes for their preparation are described, as is their use as aromatase inhibitors, for example in the treatment of cancer or as plant antifungal compounds.

2 Claims, No Drawings

DIPHENYLETHANE DERIVATIVES

This invention relates to diphenylethane derivatives possessing aromatase inhibitory and plant antifungal activity, and more particularly it relates to (azolylalkyl)-substituted diphenylethane derivatives.

United Kingdom Patent Number 1,589,852 discloses fungicidal and plant-growth regulating compounds of the general formula:

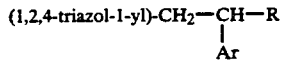

(1,2,4-triazol-1-yl)-CH$_2$—CH—R
|
Ar wherein Ar is a phenyl, mono-, di- or tri-halophenyl, lower alkylphenyl, lower alkyloxyphenyl, nitrophenyl, cyanophenyl or trifluoromethylphenyl group, and R is an alkyl group having from 1 to 10 carbon atoms, a cycloalkyl, cycloalkyl lower alkyl, lower alkenyl, aryl-lower alkyl or aryloxy-lower alkyl group, said aryl being a phenyl, naphthalenyl or substituted phenyl group, having from 1 to 3 substituents which are each independently halogen, lower alkyl, lower alkoxy, cyano, nitro or phenyl, provided that when more than one substituent is present only one thereof may be cyano, nitro or phenyl.

United Kingdom Patent Number 1,601,423 discloses systemic plant antifungal compounds of the formula

Z—(CH$_2$)$_m$—CR$^1$R$^2$—(CH$_2$)$_n$—Q wherein Z is an optionally substituted C$_6$ to C$_{10}$ aryl radical; R$_1$ (when it is not joined to R$_2$) is a cyano radical or one of the radicals defined as (2) to (8) below for R$_2$; R$_2$ (when it is not joined to R$_1$) is (1) hydrogen, (2) a C$_1$ to C$_{12}$ alkyl radical, (3) a C$_3$ to C$_8$ cycloalkyl radical, (4) a C$_2$ to C$_8$ alkenyl radical, (5) a C$_5$ to C$_8$ cycloalkenyl radical, (6) a C$_2$ to C$_8$ alkynyl radical, (7) an optionally substituted C$_6$ to C$_{10}$ aryl radical, (8) a C$_7$ to C$_{14}$ aralkyl radical which is optionally substituted in the aryl portion preferably by cyano, (9) a C$_1$ to C$_4$ alkoxy radical, (10) a C$_2$ to C$_4$ alkenyloxy radical, (11) a C$_2$ to C$_4$ alkynyloxy radical, (12) a hydroxy radical, (13) an optionally substituted C$_6$ to C$_{10}$ aryloxy radical, or (14) a C$_7$ to C$_{14}$ aralkyloxy radical which is optionally substituted in the aryl portion; or R$_1$ and R$_2$ and the carbon atom to which they are attached form a C$_3$ to C$_8$ cycloalkyl radical; m is 0 or 1; n is 1 or 2; and Q is a 1- or 4-(1,2,4-triazolyl) radical, optionally substituted.

The present invention is based upon the discovery that certain of the cyano substituted compounds comprised within the definition of the above-mentioned patents are particularly useful as aromatase inhibitors. Aromatase is an enzyme which effects aromatisation of ring A in the metabolic formation of various steroid hormones. Various cancers, for example breast cancer, are dependent upon circulating steroid hormones which have an aromatic ring A. Such cancers can be treated by surgical removal of the source of ring A aromatised steroid hormones, for example by the combination of oophorectomy and adrenalectomy. An alternative way of obtaining the same effect is by administering a chemical compound which inhibits the metabolic aromatisation of the non-aromatic steroid precursors of the aromatised steroid hormones, and the novel compounds of this invention are useful for this purpose.

According to the present invention, there is provided a diphenylethane derivative of the formula

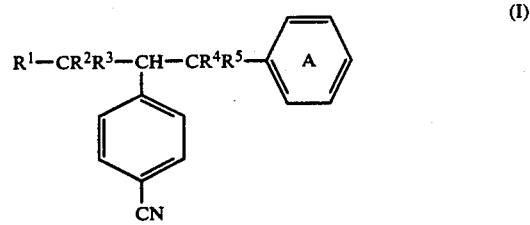

(I)

wherein R$^1$ is a heterocyclyl radical selected from 1,2,4-triazolyl, optionally substituted imidazolyl, pyridyl and pyrimidinyl radicals; R$^2$ and R$^3$, which may be the same or different, are each a hydrogen atom or a 1-6C alkyl radical; R$^4$ and R$^5$, which may be the same or different, are each a hydrogen or fluorine atom or a 1-6C alkyl radical; and A is a phenyl radical, optionally bearing one or more substituents selected from halogen atoms, cyano radicals or 1-4C halogenoalkyl or halogenoalkoxy radicals; and, for those compounds which contain a basic nitrogen atom, the pharmaceutically or veterinarily acceptable salts thereof.

A suitable value for the heterocyclyl radical R$^1$ is, for example, a 1,2,4-triazol-1-yl, 1-imidazolyl, 5-cyano, 5-methyl or 5-trifluoromethyl-1-imidazolyl, 3-pyridyl or 5-pyrimidinyl radical.

A suitable value for any of R$^2$, R$^3$, R$^4$ or R$^5$, when any of them is a 1-6C alkyl radical is, for example, a methyl, ethyl, propyl, isopropyl, butyl, isobutyl, sec-butyl, tert-butyl, pentyl or hexyl radical, and of these methyl and ethyl are preferred.

A suitable value for a halogen atom in ring A is, for example, a fluorine, chlorine or bromine atom, and of these fluorine and chlorine are preferred.

A suitable value for an optional 1-4C halogenoalkyl or halogenoalkoxy substituent in ring A is, for example, a trifluoromethyl, chlorodifluoromethyl, 1,2,2- or 2,2,2-trifluoroethyl, 2,2,3,3,3-pentafluoropropyl, 4,4,4-trifluorobutyl, trifluoromethoxy, 2,2,2-trifluoroethoxy or 4,4,4-trifluorobutoxy radical, and of these trifluoromethyl and trifluoromethoxy are preferred.

A suitable pharmaceutically or veterinarily acceptable salt is, for example, the hydrochloride, nitrate, sulphate, phosphate, acetate, lactate, citrate, maleate or fumarate.

The carbon atom bearing the substituents R$^1$, R$^2$ and R$^3$, the carbon atom bearing the 4-cyanophenyl substituent, and the carbon atom bearing the substituents R$^4$ and R$^5$, may each be asymmetrically substituted, so that the compound of the formula I may exist in racemic or optically active forms. It is common general knowledge in the art how such a racemate may be resolved into diastereoisomers, or how such diastereoisomers may be synthesized, and their aromatase inhibitory activity determined.

A preferred group of compounds of the invention comprises those diphenylethane derivatives of the formula I wherein ring A bears one or more substituents selected from chlorine atoms and cyano, trifluoromethyl and trifluoromethoxy radicals.

Particular preferred compounds of the invention are 4-[2-(4-cyanophenyl)-3-(1,2,4-triazol-1-yl)propyl]benzonitrile, 4-[1-(4-chlorobenzyl)-2-(1,2,4-triazol-1-yl)ethyl]benzonitrile, 4-[2-(1,2,4-triazol-1-yl)-1-(4-[trifluoromethyl]benzyl)ethyl]benzonitrile and 4-[2-(1,2,4- triazol-1-yl)-1-(4-[trifluoromethoxy]benzyl)ethyl]-benzonitrile.

The diphenylethane derivatives of the invention may be manufactured by processes known per se for the manufacture of chemically analogous compounds. Thus, the following processes comprise a further feature of the invention, wherein $R^1$, $R^2$, $R^3$, $R^4$, $R^5$ and A have the meanings defined above, unless otherwise stated:

(a) for those compounds wherein at least one of $R^4$ and $R^5$ is a hydrogen atom, the hydrogenation of a olefinic compound of the formula II

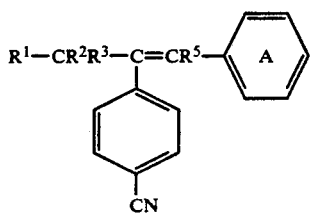

(II)

(b) for those compounds wherein at least one of $R^2$ and $R^3$ is a hydrogen atom, the hydrogenation of an olefinic compound of the formula

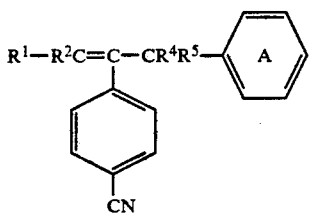

(III)

(c) the reaction of a compound of the formula

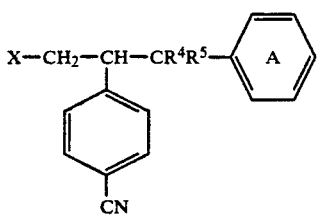

(IV)

wherein X is a known leaving group, with a heterocyclic compound of the formula $R^1H$ or with an alkali metal salt thereof.

In processes (a) and (b), the hydrogenation is preferably carried out with gaseous hydrogen in the presence of a metal catalyst such as palladium-on-carbon, platinum oxide or Raney nickel. The hydrogenation is preferably carried out at ambient temperature until uptake of hydrogen ceases.

In process (c), a suitable known leaving group X is, for example, a mesyl, tosyl or bromo group, and a suitable alkali metal salt of the heterocyclic compound of the formula $R^1H$ is, for example, a sodium salt.

The olefinic compound of the formula (II), which is used as the starting material in process (a) above, may be obtained in conventional manner, for example brominating a ketone of the formula (V) to form an alpha-bromoketone of the formula (VI), which is then reacted with a heterocyclic compound $R^1H$ or a reactive derivative thereof to form a ketone of the formula (VII). The ketone (VII) is then reacted with a Wittig reagent of the formula $Q-CR^4R^5-A$, wherein Q is a triphenylphosphine halide $(Hal^-.Ph_3P^+-)$or dialkylphosphono $[(R^6O)_2PO-]$ radical, wherein $R^6$ is a 1-6C alkyl radical, to give the required olefinic starting material.

Alternatively, the ketone (VII) may be obtained by reacting the alpha-bromoketone (VI) with 4-amino-1,2,4-triazole, followed by removal of the amino group from the product so obtained, by reaction with sodium nitrite.

The olefinic compound of the formula (III) which is used as the starting material in process (b) above may be obtained similarly by reacting a ketone of the formula VIII with a Wittig reagent of the formula $R^1-CH-R^2-Q$, wherein Q has the meaning defined above.

The compound of the formula (IV) which is used as the starting material for process (c) may be obtained by reacting a benzonitrile derivative of the formula (IX) with a compound of the formula (X) to give a dinitrile of the formula (XI), which is then selectively hydrolysed and esterified to give an ester of the formula (XII). The ester (XII) is then reduced to the corresponding alcohol (XIII), for example with lithium aluminium hydride, and the alcohol (XIII) is converted to the required starting material (IV) by reaction with mesyl or tosyl chloride or phosphorus oxybromide.

As indicated above, the compounds of the invention are useful as aromatase inhibitors. Aromatase inhibition may be demonstrated by the following tests:

DEMONSTRATION OF ACTIVITY IN VITRO

Aromatase inhibitory activity was measured using the enzyme present in the microsomal fraction of human term placenta, as described by Ryan, J. Biol, Chem. 234, 268, 1959. Enzyme activity was determined by measuring the amount of tritiated water released from 0.5 micromolar $(1\beta,2\beta-^3H)$testosterone after 20 minutes incubation at 37°. The method used was essentially that described by Thomson and Siiteri, J. Biol. Chem. 249, 5364, 1974 except that testosterone was used in place of androstenedione. Test compounds were dissolved in dimethylsulphoxide (DMSO) to achieve final concentrations of 2, 0.2 or 0.02 μg/ml. The reaction was started by the addition of 50 μl of microsome suspension to 50 μl of a solution containing substrate (testosterone) and cofactors (NADPH glucose-6-phosphate and glucose-6-phosphate dehydrogenase) and either DMSO alone or a DMSO solution of test compound. Each concentration of test compound was tested in triplicate. The reaction was stopped by the addition of 200 μl of a 5% (w/v) suspension of charcoal in 0.5% (w/v) solution of Dextran T70 in water. After 1 hour the charcoal was precipitated by centrifugation and 150 μl of supernatant removed and the amount of tritiated water present determined using a liquid scintillation counter. The number of counts in supernatant from incubations containing test compound expressed as a percentage of the counts in supernatant from incubations containing only DMSO was taken as the degree of enzyme inhibition achieved by the test compound.

DEMONSTRATION OF ACTIVITY IN VIVO

Activity in vivo was demonstrated in terms of ovulation inhibition in female rats. Daily vaginal smears were taken from rats housed under controlled lighting (lights on 06.00 hr to 20.00 hr) and those having a vaginal smear pattern consistent with 4-day ovarian cycles were selected. To these rats a single dose of test compound was given either at 16.00 hr on Day 2 of the cycle or at 12.00 hr on Day 3 of the cycle. The rats were then killed in the morning following Day 4 of the cycle—approximately 64 hours after Day 2 treatments or approximately 46 hours after Day 3 treatments—and the presence or absence of eggs in the fallopian tubes determined. The presence of eggs indicates that the rats have ovulated.

Without treatment more than 95% of rats with 4-day ovarian cycles are found to have ovulated at the time of the post-mortem examination. At an effective dose, aromatase inhibitors prevent ovulation i.e. no eggs are found in the fallopian tubes.

In the above tests, the compounds of the formula I are active at 0.5 μg/ml (in vitro) and 20 mg/kg (in vivo), and the preferred compounds of the formula I are active at 0.02 μg/ml (in vitro) and 0.1 mg/kg (in vivo).

Thus, according to a further feature of the invention, there is provided a pharmaceutical or veterinary composition comprising a diphenylethane derivative, as defined above, together with a pharmaceutically or veterinarily acceptable diluent or carrier.

The pharmaceutical or veterinary composition of the invention may be a conventional formulation for oral or parenteral administration, for example a tablet, a capsule, an emulsion or an aqueous or oily solution or suspension. The composition may contain conventional pharmaceutical excipients, and may be manufactured by conventional pharmaceutical techniques.

Preferred pharmaceutical or veterinary compositions of the invention are tablets and capsules containing from 1 to 100, preferably 5 to 50 mg. of a compound of the invention.

According to a further feature of the invention, there is provided the use of a diphenylethane derivative of the formula I wherein wherein $R^1$ is a 1,2,4-triazolyl radical, $R^2$, $R^3$, $R^4$ and $R^5$ are each a hydrogen atom, and A is a phenyl optionally bearing one or more substituents selected from halogen atoms and cyano and trifluoromethyl radicals; or, for those compounds which contain a basic nitrogen atom, a pharmaceutically or veterinarily acceptable salt thereof, in the manufacture of a pharmaceutical or veterinary composition for use as an aromatase inhibitor.

The invention is illustrated but not limited by the following Examples. Temperatures given are in degrees Celsius:

EXAMPLE 1

A mixture of 4-[1-(1,2,4-triazol-1-ylmethyl)-2-(4-trifluoromethylphenyl)vinyl]benzonitrile (0.05 g, mixed E and Z isomers) and 10% by weight palladium-on-carbon (0.02 g) in ethyl acetate (5 ml) was stirred rapidly under an atmosphere of hydrogen at atmospheric pressure for 2h. The mixture was filtered, and the filtrate was evaporated to dryness, to give 4-([2-(1,2,4-triazol-1-yl)-1-(4-trifluoromethylbenzyl)ethyl]benzonitrile as a white solid, which was washed with ethyl acetate and dried, m.p. 123°.

The starting material used in the above process was obtained as follows:

A suspension of 4-(1,2,4-triazol-1-ylacetyl)benzonitrile (1.0 g), (4-trifluoromethylbenzyl)triphenylphosphonium chloride (3.85 g), potassium tert-butoxide (1.1 g) and 18-crown-6 (1,4,7,10,13,16-hexaoxacyclooctadecane, 0.1 g) in dichloromethane (150 ml) was stirred at room temperature for 1h. Saturated ammonium chloride (100 ml) was then added, and the organic layer was separated. The aqueous layer was extracted twice with dichloromethane and the combined organic extracts were dried over sodium sulphate and evaporated to dryness, to give the mixed E and Z isomers.

EXAMPLES 2-3

The process described in Example 1 was repeated, using the appropriate 4-(substituted-vinyl)benzonitrile as starting material, to give the following compounds:

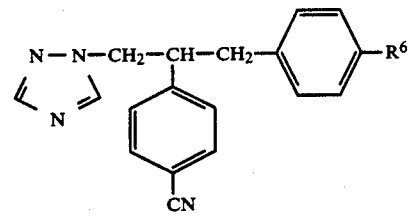

| Example | $R^6$ | M.p. |
|---|---|---|
| 2 | Cl | 118 |
| 3 | CN | 92 |

The required starting materials were obtained by processes similar to those described in the second part of Example 1.

EXAMPLE 4

The process described in Example 1 was repeated, using 4-[1-(1,2,4-triazol-1-ylmethyl)-2-(4-trifluoromethoxyphenyl)vinyl]-benzonitrile as starting material, to give 4-[2-(1,2,4-triazol-1-yl)-1-(4-trifluoromethoxybenzyl)ethyl]benzonitrile, m.p. 70°.

The starting material used in the above process may be obtained as follows:

A solution of lithium aluminium hydride in diethyl ether (1.0M, 69.4 ml) was added dropwise to a stirred solution of 4-(trifluoromethoxy)benzonitrile (6.0 g) in diethyl ether (120 ml) over 15 minutes. Water (2.66 ml), 10% sodium hydroxide solution (2.66 ml) and water (7.98 ml) were then added successively, dropwise. The precipitated solid was filtered off and washed with diethyl ether. The filtrate and washings were combined and evaporated under reduced pressure to give 4-(trifluoromethoxy)benzyl alcohol, N.M.R. in deuteriochloroform: $\delta 2.3$ (1H,s), 4.65 (2H,s), 7.2 (2H,d), 7.35 (2H,d).

A solution of this benzyl alcohol (4.0 g), triphenylphosphine (5.42 g) and carbon tetrabromide (6.86 g) in dichloromethane (75 ml) was stirred at room temperature for 30 minutes, then the reaction mixture was purified by chromatography on a silica column (Merck Art No 9385), using ethyl acetate/hexane (10/90 by volume) as eluant, to give 4-(trifluoromethoxy)benzyl bromide, N.M.R. in deuteriochloroform: $\delta 4.5$ (2H,s), 7.15 (2H,d), 7.4 (2H,d).

A solution of 4-(trifluoromethoxy)benzyl bromide (5.3 g) and triphenylphosphine (5.42 g) in acetonitrile (100 ml) was heated under reflux for 12h. The acetonitrile was evaporated under reduced pressure, and ethyl acetate (50 ml) was added to the residue. The solid material so obtained was filtered off, washed with ethyl acetate (100 ml) and dried, to give (4-trifluoromethoxybenzyl)triphenyl phosphonium bromide, N.M.R. in $d_6$-dimethylsulphoxide: $\delta 5.2$ (2H,d), 7.1 (2H,2d), 7.25 (2H,d), 7.8 (9H,m).

A suspension of (4-trifluoromethoxybenzyl)triphenyl phosphonium bromide (5.9 g), 4-(1,2,4-triazol-1-ylmethyl)benzonitrile (2.4 g), potassium tert-butoxide (1.39 g) and 18-crown-6 (0.1 g) in dichloromethane (200 ml) was stirred at room temperature for 48h. The reaction mixture was then purified by chromatography on a silica column (Merck Art No 9385), eluting with ethyl acetate, to give a mixture of the E amd Z isomers, m.p. 119° and 78° respectively.

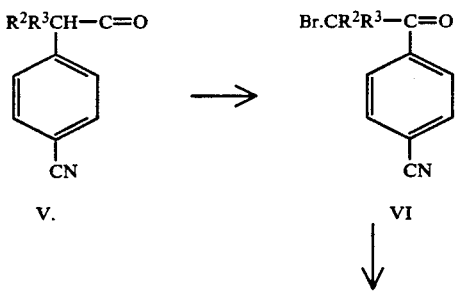

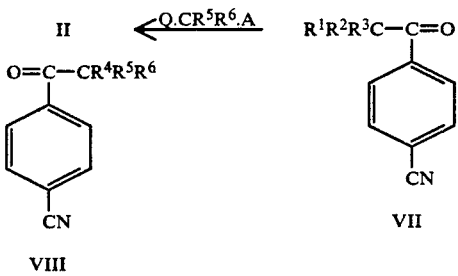

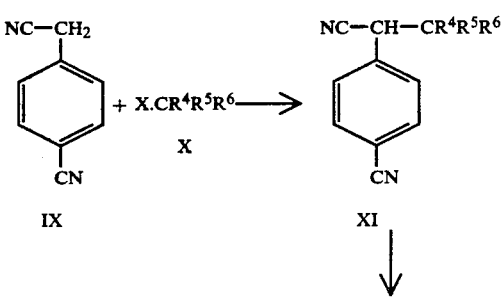

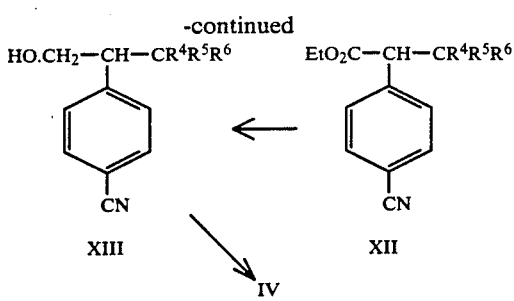

What is claimed is:

1. A pharmaceutical or veterinary composition comprising an aromatase inhibitory amount of a diphenylethane derivative of the formula

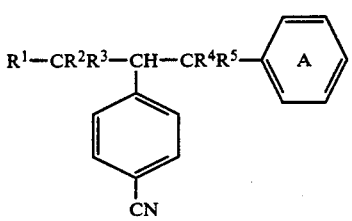

wherein $R^1$ is a 1,2,4-triazolyl; $R^2$ and $R^3$, which may be the same or different, are each a hydrogen atom or a 1-6C alkyl radical; $R^4$ and $R^5$, which may be the same or different, are each a hydrogen or fluorine atom or a 1-6C alkyl radical; and A is a phenyl radical, optionally bearing one or more substituents selected from halogen atoms, cyano radicals or 1-4C halogenoalkyl or halogenoalkoxy radicals; and, for those compounds which contain a basic nitrogen atom, the pharmaceutically or veterinarily acceptable salts thereof, together with a pharmaceutically or veterinarily acceptable diluent or carrier.

2. A method of treating steroid hormone dependent tumors which comprises administering to a host in need of such treatment an effective aromatase inhibitory amount of a diphenylethane derivative of the formula

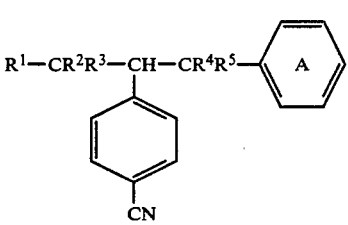

wherein $R^1$ is a 1,2,4-triazolyl; $R^2$ and $R^3$, which may be the same or different, are each a hydrogen atom or a 1-6C alkyl radical; $R^4$ and $R^5$, which may be the same or different, are each a hydrogen or fluorine atom or a 1-6C alkyl radical; and A is a phenyl radical, optionally bearing one or more substituents selected from halogen atoms, cyano radicals or 1-4C halogenoalkyl or halogenoalkoxy radicals; and, for those compounds which contain a basic nitrogen atom, the pharmaceutically or veterinarily acceptable salts thereof.

* * * * *